(12) United States Patent
Yamashita et al.

(10) Patent No.: US 9,284,289 B2
(45) Date of Patent: Mar. 15, 2016

(54) METHOD FOR PRODUCING TETRAHYDROFURAN

(71) Applicant: MITSUBISHI CHEMICAL CORPORATION, Tokyo (JP)

(72) Inventors: Ryo Yamashita, Mie (JP); Seijiro Nishimura, Mie (JP); Hisashi Nagahama, Mie (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/689,562

(22) Filed: Apr. 17, 2015

(65) Prior Publication Data

US 2015/0218117 A1 Aug. 6, 2015

Related U.S. Application Data

(63) Continuation of application No. PCT/JP2013/078163, filed on Oct. 17, 2013.

(30) Foreign Application Priority Data

Oct. 18, 2012 (JP) ................................. 2012-231016
Jan. 29, 2013 (JP) ................................. 2013-014415

(51) Int. Cl.
 *C07D 307/08* (2006.01)
(52) U.S. Cl.
 CPC .................................... *C07D 307/08* (2013.01)

(58) Field of Classification Search
 CPC ..................................................... C07D 307/08
 USPC ........................................................... 549/509
 See application file for complete search history.

(56) References Cited

U.S. PATENT DOCUMENTS

| 4,665,205 A * | 5/1987 | Yamada ............... C07D 307/08 |
| | | 549/509 |
| 6,316,640 B1 | 11/2001 | Fischer et al. |
| 2006/0122365 A1 | 6/2006 | Pinkos et al. |
| 2014/0179935 A1 | 6/2014 | Izawa et al. |

FOREIGN PATENT DOCUMENTS

| JP | 61-126080 | 6/1986 |
| JP | 10-077277 | 3/1998 |
| JP | 2002-526485 | 8/2002 |
| JP | 2004-107619 | 4/2004 |
| JP | 2006-503050 | 1/2006 |
| JP | 2012-219066 | 11/2012 |
| JP | 2012-250966 | 12/2012 |
| JP | 2012-250967 | 12/2012 |
| JP | 2013-116881 | 6/2013 |

OTHER PUBLICATIONS

International Search Report issued Jan. 14, 2014 in PCT/JP2013/078163 filed Oct. 17, 2013.

* cited by examiner

*Primary Examiner* — Golam M M Shameem
(74) *Attorney, Agent, or Firm* — Oblon, McClelland, Maier & Neustadt, L.L.P.

(57) ABSTRACT

The present invention relates to a method for producing tetrahydrofuran, comprising feeding 1,4-butanediol to a reactor and performing a cyclodehydration reaction in the presence of an acid catalyst to obtain tetrahydrofuran, in which a water concentration in a in-reactor liquid phase is within a range of 1.4 to 10 wt %.

15 Claims, 1 Drawing Sheet

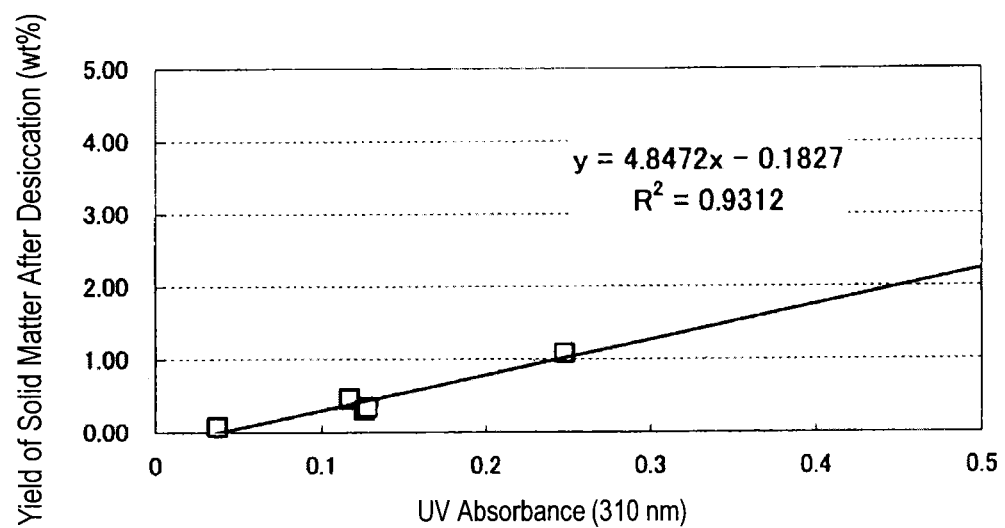

METHOD FOR PRODUCING TETRAHYDROFURAN

TECHNICAL FIELD

The present invention relates to a method for producing tetrahydrofuran. More specifically, the present invention relates to a method for producing tetrahydrofuran by a cyclodehydration reaction using 1,4-butanediol as a raw material and using an acid catalyst in particular.

BACKGROUND ART

Tetrahydrofuran (hereinafter, sometimes simply referred to as "THF") has been heretofore used as a solvent for various organic compounds and in addition, is known to be a compound useful also as a raw material monomer of a polyether polyol such as polytetramethylene ether glycol.

As the industrial production method of a cyclic ether such as tetrahydrofuran, a variety of production methods are known. Among others, the cyclic ether is produced in many cases by performing a cyclodehydration reaction of a dihydroxy compound. In this cyclodehydration reaction of a dihydroxy compound, an acid catalyst exhibiting a high conversion ratio and a high selectivity is generally used as the catalyst. For example, Patent Document 1 describes a method of dehydrogenating and dehydrating an alkanediol such as 1,4-butanediol (hereinafter, sometimes simply referred to as "1,4BG") in the presence of a cobalt-containing catalyst, an organic sulfonic acid and a high-boiling-point amine to produce an $\alpha,\beta$-cyclic unsaturated ether such as dihydrofuran. In addition, Patent Document 2 describes a method for continuously producing THF by a reaction of a 1,4-butanediol-containing reaction mixture on a heteropolyacid catalyst. The reactor type when performing a cyclodehydration reaction of 1,4BG by using such a catalyst to produce THF includes, for example, a liquid phase reactor using a fixed bed reactor, and a reaction distillation type where the product is distilled off from the reactor through a vapor phase portion.
Background Art Document
Patent Document Patent Document 1: JP-A-10-77277 (the term "JP-A" as used herein means an "unexamined published Japanese patent application")

Patent Document 2: JP-T-2006-503050 (the term "JP-T" as used herein means a published Japanese translation of a PCT patent application)

SUMMARY OF INVENTION

Problem that Invention is to Solve

In the method described in Patent Document 1 or 2, there is a fear that catalyst deterioration, equipment corrosion, etc. may occur depending on the reaction conditions, and many restrictions are imposed on the operation conditions. In addition, since the catalyst is expensive and in turn, the equipment or operation cost is high, the method cannot be an sufficiently advantageous method in industry.

The cyclodehydration reaction of 1,4BG by an acid catalyst described in Patent Document 2 is subject to a reaction-inhibiting effect of water, and the production rate of tetrahydrofuran is liable to decrease in the presence of byproduct water produced by the reaction.

Therefore, when performing a cyclodehydration reaction of 1,4BG in the presence of an acid catalyst, the cyclodehydration reaction of 1,4BG is continuously carried out by reducing the water concentration in the reactor as much as possible, but this is found to raise a problem that precipitation of a solid byproduct increases along with the rise in liquid viscosity in the reactor and due to the presence of a solid byproduct attached to an inner wall of reactor or pipe, THF cannot be continuously produced for a long period of time.

Furthermore, in the method described in Patent Document 2, water causes a hindrance to progress of the cyclodehydration reaction and when a large amount of byproduct water produced by the cyclodehydration reaction is present, the THF production rate readily decreases.

Therefore, in order to keep maintaining the intended production amount of THF, the cyclodehydration reaction of 1,4BG had to be continuously performed by reducing the water concentration in the reactor as much as possible, thereby preventing a decrease in the THF production rate. However, it has been revealed that if the water concentration in the reactor is too low, precipitation of a solid byproduct increases along with the rise in liquid viscosity in the reactor and THF cannot be continuously produced or THF obtained after the reaction above contains a large amount of 2,3-dihydrofuran (hereinafter, sometimes simply referred to as "2,3DHF").

When a large amount of 2,3DHF is contained in THF, not only the purity of THF decreases but also, for example, at the time of production of a polyether polyol such as polytetramethylene ether glycol by using 2,3DHF-containing THF as a raw material, 2,3DHF forms a polymer in the production process to cause coloration. Therefore, 2,3DHF is preferably prevented from mixing in THF and is preferably removed in advance.

However, 2,3DHF is close in boiling point to THF and difficult to separate and remove by distillation and in general, must be removed, for example, by a method involving conversion to a high-boiling component by a hydration treatment using an ion-exchanged resin, etc. and then separation by distillation, or a method involving hydrogenation by a catalyst containing Pd and Ni, but when a large amount of 2,3DHF is produced in the reactor, the equipment or catalyst used for removal is burdened with a load, as a result, the load for THF purification rises.

The present invention has been made under these circumstances, and an object of the present invention is to provide a method for producing THF from 1,4-butanediol by using an acid catalyst, in which reduction in the reaction rate can be suppressed and attachment to an inner wall of a reactor or clogging of a pipe due to precipitation of a solid byproduct can be prevented and which is thus an industrially advantageous production method of THF.

Another object of the present invention is to provide a method for producing THF from 1,4-butanediol by a reaction distillation method using an acid catalyst, in which precipitation of a solid byproduct can be suppressed even in continuous production of THF, production of 2,3DHF can be reduced, and the load for THF purification in a later process after THF production can be decreased and which is thus an industrially advantageous production method of THF.

Means for Solving Problem

As a result of intensive studies to solve the above-described problems, the present inventors focused on the fact that 2-(4-hydroxybutoxy)-tetrahydrofuran (hereinafter, sometimes simply referred to as "BGTF") contained in the raw material 1,4BG and water are correlated with the rise in liquid viscosity in a reactor and the precipitation of a solid byproduct, and have found that when the water concentration in the reactor liquid phase and the amount of BGTF fed to the reactor are adjusted to certain ranges, THF is stably obtained while suppressing precipitation of a solid byproduct even in continuous production and keeping the reduction in the reaction rate to a minimum. The present invention have been attained based on this finding.

In addition, the present inventors elucidated that 2-hydroxytetrahydrofuran (hereinafter, sometimes simply referred to as "OTF") produced by the reaction of BGTF contained in the raw material 1,4BG with byproduct water produced in a reactor is one of substances responsible for precipitation of a solid byproduct in a reactor and furthermore, the concentration of OTF is correlated with the production amount of 2,3DHF, and have found that when the OTF concentration in the reactor liquid phase is controlled to a specific range, THF is stably obtained while suppressing precipitation of a solid byproduct in the reactor and reducing the production amount of 2,3DHF. The present invention has been attained based on this finding.

The gist of the present invention resides in the following production method of tetrahydrofuran.

[1] A method for producing tetrahydrofuran, comprising feeding 1,4-butanediol to a reactor and performing a cyclodehydration reaction in the presence of an acid catalyst to obtain tetrahydrofuran, wherein a water concentration in a in-reactor liquid phase is within a range of 1.4 to 10 wt %.

[2] A method for producing tetrahydrofuran, comprising feeding 1,4-butanediol containing 2-(4-hydroxybutoxy)-tetrahydrofuran to a reactor and performing a cyclodehydration reaction in the presence of an acid catalyst to obtain tetrahydrofuran, wherein a θ value of the following formula (1) is within a range of 0.001 to 0.5:

$$\theta = B/(W \cdot T) \quad (1)$$

(in formula (1), T represents a reaction time (hr), B represents a cumulative weight (g) of 2-(4-hydroxybutoxy)-tetrahydrofuran in the reaction time T, and W represents an in-reactor liquid-phase water weight (g) in the reaction time T).

[3] A method for producing tetrahydrofuran, comprising feeding 1,4-butanediol to a reactor and performing a cyclodehydration reaction in the presence of an acid catalyst to obtain tetrahydrofuran, wherein the cyclodehydration reaction is performed by a reaction distillation method and a 2-hydroxytetrahydrofuran concentration in the in-reactor liquid phase is within a range of 500 ppm by weight or less.

[4] The method for producing tetrahydrofuran as described in any one of the above [1] to [3], wherein said 1,4-butanediol contains from 0.001 to 5.0 wt % of 2-(4-hydroxybutoxy)-tetrahydrofuran.

[5] The method for producing tetrahydrofuran as described in the above [1] or [2], wherein the cyclodehydration reaction is performed by a reaction distillation method.

[6] The method for producing tetrahydrofuran as described in any one of the above [1] to [5], wherein said acid catalyst has a pKa value of 4 or less.

[7] The method for producing tetrahydrofuran as described in any one of the above [1] to [6], wherein said acid catalyst is a homogeneous acid catalyst.

[8] The method for producing tetrahydrofuran as described in any one of the above [1] to [7], wherein the acid catalyst concentration in said reactor liquid phase is controlled to a range from 0.01 to 20 wt %.

[9] The method for producing tetrahydrofuran as described in any one of the above [1] to [8], wherein the temperature of the liquid phase portion in said reactor is within a range of 80 to 250° C.

[10] The method for producing tetrahydrofuran as described in any one of the above [1] to [9], wherein said acid catalyst is an organic sulfonic acid.

[11] The method for producing tetrahydrofuran as described in any one of the above [1] to [10], further comprising a step of dissolving said acid catalyst having a pKa value of 4 or less in 1,4-butanediol, tetrahydrofuran or water and feeding the solution to the reactor.

[12] The method for producing tetrahydrofuran as described in any one of the above [1] to [11], wherein the viscosity at 25° C. of the solution of the liquid phase portion in said reactor is within a range of 50 to 1,300 mPa·s.

[13] The method for producing tetrahydrofuran as described in any one of the above [2] to [12], wherein the water concentration in the liquid phase in said reactor is within a range of 1.4 to 10 wt %.

[14] The method for producing tetrahydrofuran as described in any one of the above [1] to [13], wherein a gas containing tetrahydrofuran and water and existing in the vapor phase in said reactor is drawn out to outside the reactor.

[15] The method for producing tetrahydrofuran as described in any one of the above [3] to [14], wherein a gas containing tetrahydrofuran, water and 2-hydroxytetrahydrofuran and existing in the vapor phase in said reactor is withdrawn to the outside of the reactor.

[16] The method for producing tetrahydrofuran as described in the above [15], wherein at the time of withdrawal of said 2-hydroxytetrahydrofuran to the outside of the reactor, the ratio of the concentration by weight of 2-hydroxytetrahydrofuran contained in the vapor phase to the concentration by weight of 2-hydroxytetrahydrofuran contained in the liquid phase is within a range of 10 to 70%.

[17] The method for producing tetrahydrofuran as described in the above [15] or [16], wherein at the time of withdrawal of said 2-hydroxytetrahydrofuran to the outside of the reactor, the reflux ratio of the distillation column is set to within a range of 0.01 to 4.0 by using a reactor of a reaction distillation type.

Advantageous Effects of Invention

According to the present invention, tetrahydrofuran can be continuously produced from 1,4-butanediol with good efficiency while reducing the production of a solid byproduct and at the same time, avoiding reduction in the reaction rate.

In addition, by using the production method of THF according to the present invention, the production amount of 2,3DHF can be reduced while suppressing precipitation of a solid byproduct in a reactor. In turn, a continuous operation over a long period of time becomes feasible and furthermore, the load for THF purification decreases, so that THF can be produced with higher efficiency than ever before.

BRIEF DESCRIPTION OF DRAWINGS

FIG. 1 is a graph showing the relationship between the UV spectrum value of the solution in the reactor liquid phase and the yield of solid matter obtained by a desiccation treatment in Reference Examples 1 to 5.

DESCRIPTION OF EMBODIMENTS

The following description is one example (representative example) of the embodiment of the present invention, and the present invention is limited to the contents therein.

Here, "mass %", "ppm by mass" and "parts by mass" have the same meanings as "wt %", "ppm by mass" and "parts by weight", respectively. In addition, when referred to merely as "ppm", this indicates "ppm by weight".

The raw material 1,4BG for use in the present invention can be obtained by a known method. For example, 1,4BG obtained by hydrogenation and hydrolysis of 1,4-diacetoxy-2-butene that is obtained by diacetoxylation of butadiene, may be used. Alternatively, for example, 1,4BG obtained by hydrogenation of maleic anhydride, 1,4BG derived from acetylene by the Reppe process, 1,4BG obtained through oxidation of propylene, or 1,4BG obtained by a fermentation process can be used. 1,4BG produced by these known techniques contains, as a byproduct occurring in the production process, impurities such as 1-acetoxy-4-hydroxybutane, dehydrated dimer or trimer of 1,4BG, gamma butyrolactone and 2-methyl-1,3-propanediol, but these impurities may be contained in the raw material 1,4BG for use in the present invention.

In addition, since BGTF is produced resulting from oxidation of 1,4BG, BGTF is generally contained in 1,4BG obtained by the above-described production methods or the commercially available 1,4BG. Therefore, when using it as a raw material for the production of THF, this 1,4BG is purified by a known method such as hydrogenation and distillation to reduce the contents of various impurities such as BGTF and then used.

<Production Method 1>

In the present invention, the raw material 1,4BG may contain from 0.001 to 5.0 wt % of BGTF. The concentration of BGTF contained in the raw material 1,4BG for use in the present invention is preferably from 0.001 to 1.0 wt %, more preferably from 0.01 to 0.8 wt %, still more preferably from 0.02 to 0.5 wt %.

If the concentration of BGTF in the raw material 1,4BG is too low, the purification requires a great deal of cost, leading to an industrially undesirable tendency, whereas if the concentration of BGTF in the raw material 1,4BG is too high, solid matter may precipitate and attach to the reactor to inhibit the continuous operation.

In the present invention, in order to reduce the production of a solid byproduct in the reactor and stably obtain THF while keeping the reduction in the reaction rate to a minimum, it is necessary to use BGTF-containing 1,4BG as a raw material, adjust the water concentration in the reactor liquid phase to a range from 1.4 to 10 wt %, and/or control the θ value of the following formula (1) to a range from 0.001 to 0.5. Under such conditions, a polymerization product accumulated at a high concentration in the reactor can dissolve in the reactor liquid phase without causing precipitation, and the operation can be stably continued for a long period of time.

$$\theta = B/(W \cdot T) \quad (1)$$

(In formula (1), T represents a reaction time (hr), B represents a BGTF cumulative weight (g) in the reaction time T, and W represents an in-reactor liquid-phase water weight (g) in the reaction time T.)

Definitions in formula (1) are described below.

The reaction time (T) is the elapsed time from the reaction start time that is assumed as the time where a raw material and a catalyst are introduced into a reactor and the temperature in the reactor reaches a preset temperature.

The BGTF cumulative weight (g) (B) in the reaction time T is the product of the weight of the raw material 1,4BG introduced in the reaction time (T) and the BGTF concentration in the raw material 1,4BG. In the case where the raw material is separately prepared in the reactor, the cumulative weight is the sum of the BGTF weight in the raw material prepared in the reactor and the BGTF weight in the raw material introduced.

The in-reactor liquid-phase water weight (g) (W) in the reaction time T is the weight of water contained in the liquid phase in the reactor and is the product of the total weight of the liquid-phase moiety in the reactor and the water concentration measured on the liquid phase moiety in the reaction time (T) by using the Karl Fischer method. In the case where water is present in the liquid phase portion and vapor phase portion in the reactor, the weight means the water weight of the liquid phase in the reactor.

BGTF in 1,4BG is a cyclic acetal produced by the reaction of 4-hydroxybutylaldehyde and 1,4BG and is easily decomposed under acidic conditions and easily polymerized through 2,3-dihydrofuran, 2-hydroxy-tetrahydrofuran or 4-hydroxybutylaldehyde. The polymer (acetal polymer) produced here contains many hydroxyl groups as a functional group and is a kind of polyfunctional polyol.

In the reactor, THF is produced by a cyclodehydration reaction of the raw material 1,4BG and, as other byproducts, a dimer or trimer of 1,4BG and an intermolecular dehydrated polymer having a molecular weight of approximately from 100 to 10,000 (1,4BG oligomer), resulting from a side reaction, i.e., intermolecular dehydration of 1,4BG, are also present. Such a byproduct is accumulated to a high concentration in the reactor due to performing the cyclodehydration reaction of 1,4BG for a long period of time. All of the acetal polymer, 1,4BG oligomer and raw material 1,4BG are highly hydrophilic and can be dissolved in the reactor liquid phase by adjusting the water concentration in the reactor liquid phase to a range from 1.4 to 10 wt % and/or controlling the value of θ of formula (1) to a range from 0.001 to 0.5, so that the operation can be stably continued for a long period of time.

If the water concentration in the reactor liquid phase is less than 1.4 wt %, a dehydration reaction of the acetal polymer readily proceeds, and a carbon-carbon conjugated double bond is produced. With further progress of the dehydration reaction, the acetal polymer is deprived of a hydrophilic functional group and becomes a hydrophobic polymer, as a result, solid matter precipitates in the reactor. By adjusting the water concentration in the reactor liquid phase to 1.4 wt % or more, the dehydration reaction of the acetal polymer is notably suppressed. The lower limit of the water concentration in the reactor liquid phase is preferably 1.5 wt %, more preferably 2.0 wt %.

On the other hand, if the water concentration in the reactor liquid phase exceeds 10 wt %, water exerts an inhibitory effect on the cyclodehydration reaction, and the THF production rate significantly decreases. Therefore, the upper limit of the water concentration in the reactor liquid phase is 10 wt %, preferably 8 wt %, more preferably 7 wt %.

Furthermore, in the present invention, the water weight in the reactor liquid phase is set to a specific range relative to the reaction time-based average of the cumulative feed weight of BGTF contained in the raw material 1,4BG fed to the reactor, whereby the dissolved state in the reactor liquid phase can be maintained without allowing a polymerization product accumulated at a high concentration in the reactor to precipitate as solid matter and the operation can be stably continued for a long period of time. When the concentration of BGTF in the raw material 1,4BG is high, precipitation of solid matter can be suppressed by increasing the water concentration in the reactor liquid phase, whereas when the concentration of BGTF in 1,4BG is low, the cyclodehydration reaction can be advantageously advanced by decreasing the water concentration in the reactor liquid phase.

The θ value represented by formula (1) is from 0.001 to 0.5, preferably from 0.002 to 0.4, more preferably from 0.005 to 0.35. As the value is larger, a dehydration reaction of the acetal polymer proceeds in a short-time operation to readily cause precipitation of solid matter in the reactor, and as the value is smaller, the production rate of THF decreases due to the reaction-inhibiting effect of water.

In the present invention, adjusting the water concentration in the reactor liquid phase to a specific range or controlling the value of formula (1) to a specific range means that when the reaction start time is assumed as the time where a raw material and a catalyst are introduced into a reactor and the temperature in the reactor reaches a preset temperature and the reaction stop time is assumed as the time where the temperature in the reactor is stopped being maintained at the preset temperature (the time where heating is stopped), the operation in the portion of 70% or more of the total reaction time from the reaction start time to the reaction stop time is carried out under any one of the conditions specified above.

The specific method for adjusting the water concentration in the reactor liquid phase to a range from 1.4 to 10 wt % and/or controlling the value of formula (1) to a range from 0.001 to 0.5 is not particularly limited, but, for example, the below-described methods may be used. For example, in the case of using a flow reaction apparatus or a batch reaction apparatus, the water amount can be controlled by adding water to the raw material.

In the case of using a reaction distillation apparatus, the reaction temperature or various conditions are controlled to change the rate of water production resulting from cyclodehydration of 1,4BG in the reactor liquid phase or the distribution coefficient based on the vapor-liquid equilibrium of water between the liquid phase portion and the vapor phase portion in the reactor, whereby the water amount in the reactor can be controlled to a specific range. In addition, the reflux ratio of a liquid obtained by discharging a gas containing THF produced by the reaction and water from the vapor phase portion of the reactor and condensing the gas by a heat exchanger is controlled to change the flow rate ratio between THF and water drawn out to outside the reactor, whereby water less volatile than THF can be retained in the reactor and the water amount can be controlled to a specific range. Furthermore, the water amount can also be controlled to a specific range by continuously or intermittently supplying water from outside the system. The water supplied from outside the system is not particularly limited, but byproduct water obtained by further distilling and separating THF produced by the reaction from water is preferably circulated and reused, because the amount of waste water is not increased.

In the present invention, the method for confirming the water amount in the in-reactor liquid phase is not particularly limited but includes, for example, a method of confirming the water concentration by using the Karl Fischer method for the liquid phase moiety in the reactor, and a method of balancing and calculating the water amount in the in-reactor liquid phase from the water amount in the raw material and the water amount in the product drawn out to outside the reactor.

The production level of a carbon-carbon conjugated system due to dehydration of the acetal polymer can be confirmed from the UV spectrum of the reactor liquid phase. The measurement wavelength region is not particularly limited but is preferably one or more wavelengths selected from the range of 300 to 330 nm at the time of operation for a short time of about 100 hours, and one or more wavelengths selected from the range of 650 to 750 nm at the time of operation for a long time. To rise in the absorbance at a specific wavelength is to prove the growth of a carbon-carbon conjugated system and indicates that a dehydration reaction of the acetal polymer readily proceeds and precipitation of solid matter is likely to develop in the reactor.

The method for more quantitatively determining the production level of the carbon-carbon conjugated system due to dehydration of the acetal polymer from the UV spectrum includes a method where each of solutions in the reactor liquid phases having different absorbances is heated and a linear approximate equation of UV spectral value-solid matter quantity is prepared from the weight of the obtained dry solid matter.

From the concentration of solid matter contained in the in-reactor liquid phase and the solubility of solid matter, which are obtained by the approximate equation above, the time until the concentration of solid matter contained in the in-reactor liquid phase is saturated by exceeding the solubility of solid matter at an arbitrarily set temperature in the reactor, that is, the precipitation start time, can also be calculated. In the present invention, the precipitation start time is usually 4 hours or more, preferably 5 hours or more, more preferably 10 hours or more, still more preferably 13 hours of more. If the precipitation start time is too short, inhibition of the reaction, fouling of the heat exchanger, or clogging of the pipe due to precipitation of solid matter, sometimes makes the continuous operation difficult.

In the method where, as in the present invention, THF is produced by performing a cyclodehydration reaction of 1,4BG in the presence of an acid catalyst, the reaction mode employed may be a known reaction mode such as flow reaction mode, batch reaction mode and reaction distillation mode.

Among others, a reaction distillation method where a catalyst is caused to exist in a reaction part, 1,4 BG is fed to the reaction part, THF produced by a cyclodehydration reaction and a byproduct containing water and OTF are drawn out from the vapor phase portion of the reactor, and the liquid phase portion is kept in a state containing remaining water, a byproduct and an unreacted raw material, is preferably used, because the water amount in the reactor can be easily controlled by the temperature setting or setting of various conditions.

As the reaction mode when producing THF of the present invention, a known reaction mode such as flow reaction mode, batch reaction mode and reaction distillation mode can be used. A reaction distillation mode where the water amount in the reactor is easily controlled by the temperature setting or setting of various conditions, is preferred.

The reactor employed in the production of THF of the present invention is used interchangeably with a reaction tank, a reaction vessel, a reaction oven, a reaction column, etc. and is not particularly limited as long as it is a vessel capable of performing a cyclodehydration reaction. In the case where the cyclodehydration reaction reaches chemical equilibrium, the reaction is allowed to proceed by removing water produced by the reaction from the reactor and therefore, the reactor preferably has a structure including therein an in-reactor liquid phase portion where a raw material, a catalyst or a product is present in liquid phase to perform a reaction, and a vapor phase portion composed of a highly volatile product.

The product is drawn out from the vapor phase portion to outside the reactor according to the progress of reaction, whereby the reaction proceeds. In the reaction where, as in the present invention, THF is produced by performing a cyclodehydration reaction of 1,4BG in the presence of an acid catalyst, a catalyst is caused to exist in a reaction part, 1,4 BG is fed to the reaction part, volatilized THF produced by the reaction and a part of water vapor are contained in the vapor phase portion of the reaction part, and remaining water and a byproduct are contained in the liquid phase portion.

The catalyst for use in the present invention is not particularly limited as long as it is an acid catalyst, but an acid catalyst having a pKa value of 4 or less is preferably used. The acid catalyst includes, usually, a heterogeneous acid catalyst such as cation exchange resin, sulfonated zirconia and fluorosulfonic acid-containing resin (e.g., Nafion (registered trademark, DuPont)), and a homogeneous catalyst such as sulfuric acid, nitric acid, phosphoric acid, heteropolyacid (phosphotungstic acid, phosphomolybdic acid, silicotungstic acid) and sulfonic acid compound, and a homogeneous catalyst is preferably used. Among homogeneous catalysts, from the standpoint that the catalytic activity or use temperature range is wide and the handling is easy and simple, a sulfonic acid is more preferred, and an organic sulfonic acid is most preferred. Specific examples of the organic sulfonic acid include an aromatic sulfonic acid derivative such as para-toluenesulfonic acid, benzenesulfonic acid, ortho-toluenesulfonic acid and meta-toluenesulfonic acid, and a chain hydrocarbon sulfonic acid derivative such as methanesulfonic acid, butanesulfonic acid, hexanesulfonic acid, octanesulfonic acid and nonanesulfonic acid. These acids may be used singularly or plurally or may contain, in the carbon skeleton, a functional group other than a sulfonic acid. Among these specific examples, para-toluenesulfonic acid is preferred.

Incidentally, the reaction may be started by previously causing the catalyst to exist in the reaction part of the reactor before feeding the raw material 1,4BG and starting the reaction, but from the standpoint of suppressing the reduction in the reaction yield due to deterioration of the catalyst, it is more effective to successively charge the catalyst into the reactor. Among these, the catalyst is preferably dissolved in water, 1,4BG or THF and intermittently or continuously fed to the reactor by supplying the solution into the reactor.

As for the cyclodehydration reaction in the production of THF of the present invention, the reaction is performed while heating the reactor, and the heating system of the reactor may be a system where a heat medium such as steam is brought into contact with an external jacket to perform heating or may be a system where a heat transfer device such as coil is provided inside the reactor to perform heating. The heating system may also be a system where a heat exchanger is provided outside the reactor and the liquid phase portion of the reactor is partially drawn out to outside the system, then heated by the heat exchanger and again returned to the reactor, thereby performing heating. The material for the interior of such a reactor or heat exchanger is not particularly limited, and a known material may be used, but the material includes SUS, Hastelloy (registered trademark), titanium, and glass. Among these, from the standpoint that corrosion due to sulfur contained in sulfonic acid can be reduced, SUS304, SUS316, SUS316L, SUS317, SUS317L, SUS329J4L, Hastelloy (registered trademark), titanium, and glass are preferred, and SUS316L, SUS317L, SUS329J4L, Hastelloy (registered trademark), etc. are more preferred.

In the reactor for use in the present invention, an agitator for uniformly and efficiently performing the cyclodehydration reaction is preferably provided. A mixing method equivalent to an agitator may also be used as long as the reactivity is not impaired. The agitator is not particularly limited but usually consists of an electric motor, a shaft and a stirring blade, and the stirring blade is not limited in its shape. The mixing method equivalent to an agitator is also not particularly limited and includes, for example, a method where a gas inert to the reaction is supplied to the liquid phase portion, a method where the liquid phase portion of the reaction solution is partially drawn out to outside the system and again returned to the reactor, and a mixing method utilizing convection inside the reactor.

In the vapor phase portion of the reactor, a gas containing THF produced in the reaction part inside the reactor and water is present, and the gas may be introduced into a heat exchanger and condensed/liquefied in the heat exchanger to obtain a condensate containing tetrahydrofuran and water. The heat exchanger above is a device for condensing/liquefying a distillate occurring from the reactor, and the condensation/liquefaction is performed by exchanging heat between the distillate and an external fluid that is a cooling liquid. Incidentally, the gas containing THF and water may contain product water from a raw material charged in the form of an aqueous solution, a dehydration solvent used, if desired, for azeotroping with product water, and the like.

Incidentally, a distillation column, such as packed column and plate column, for separating high-boiling-point components, such as raw material 1,4-butanediol, from the gas containing produced THF and water may be provided before introduction into a heat exchanger. The number of plates of the packed column, plate column, etc. may be arbitrary but is usually, in terms of theoretical plates, 1 or more, preferably 3 or more, and usually 100 or less, preferably 20 or less, more preferably 5 or less, still more preferably 4 or less. If an excessively large number of theoretical plates are used, the column becomes too large, and the economic efficiency for construction of the facility may be reduced.

The material for the interior of such a distillation column or heat exchanger is not particularly limited and a known material may be used, but since corrosion by an acid catalyst is lesser compared to the reactor, the material includes SUS304, SUS316, SUS316L, etc.

In the case of performing the present invention by using a reaction distillation apparatus, it is preferred that a gas containing produced THF and water is discharged from the vapor phase portion of the reactor and condensed by a heat exchanger and a condensate is obtained from the outlet of the heat exchanger and partially returned to the vapor phase portion in the reactor. The composition of the condensed liquid contains THF and water at arbitrary concentrations, but the THF concentration is usually from 30 to 99 wt %, preferably from 30 to 95 wt %, more preferably from 50 to 85 wt %, still more preferably from 50 to 75 wt %. In addition, the cyclodehydration reaction of the present invention produces water stoichiometrically, and the water concentration in the condensate is usually from 1 to 50 wt %, preferably from 5 to 30 wt %, more preferably from 15 to 25 wt %.

While the condensate obtained from the outlet of the heat exchanger is partially returned to the vapor phase portion in the reactor, the remaining condensate is drawn out to outside the reactor, and the ratio of the flow rate of the condensate drawn out to outside the reactor to the flow rate of the condensate fed to the vapor phase portion of the reactor (hereinafter, sometimes referred to as "reflux ratio") is usually 0.001 or more, preferably 0.01 or more, more preferably 0.05 or more, still more preferably 0.8 or more, yet still more preferably 1.0 or more. The lower limit is usually 30 or less, preferably 10 or less, more preferably 4.0 or less, still more preferably 3.0 or less, yet still more preferably 1.0 or less, and most preferably 0.8 or less. If the reflux ratio is too high, the cost of a heat source for heating is increased to deteriorate the economic efficiency, whereas if the reflux ratio is too low, the effect of suppressing precipitation of solid matter in the reactor is not obtained and at the same time, mixing of a high-boiling-point component into the condensate tends to proceed due to poor separation. The temperature at the time of introduction of a gas containing THF and water into the heat exchanger is usually from 10 to 200° C., preferably from 60 to 100° C.

In other words, when the condensate obtained from the outlet of the heat exchanger is partially returned to the vapor phase portion in the reactor and the remaining condensate is drawn out to outside the reactor, the ratio of the flow rate of the condensate fed to the vapor phase portion of the reactor to the flow rate of the condensate drawn out to outside the reactor (hereinafter, sometimes referred to as "reflux ratio") is usually from 0.001 to 30, preferably from 0.01 to 10.00, more preferably from 0.1 to 3.0. If the reflux ratio is too high, the cost of a heat source for heating is increased to deteriorate the economic efficiency, whereas if the reflux ratio is too low, the effect of suppressing precipitation of solid matter in the reactor is not obtained and at the same time, mixing of a high-boiling-point component into the condensate tends to proceed due to poor separation. The temperature at the time of introduction of a gas containing THF and water into the heat exchanger is usually from 10 to 200° C., preferably from 60 to 100° C.

In the present invention, the reaction of producing THF by cyclodehydration of 1,4BG proceeds in the reaction part in the reactor, and the concentration of the catalyst in the liquid phase portion in the reactor is usually from 0.01 to 20 wt %, preferably from 0.05 to 10 wt %, more preferably from 0.2 to 5 wt %.

The viscosity at 25° C. of the solution in the liquid phase portion in the reactor is usually from 50 to 1,300 mPa·s, preferably from 100 to 1,000 mPa·s. The measuring method is described later.

The temperature of the liquid phase portion in the reactor is preferably from 80 to 250° C., more preferably from 100 to 200° C., still more preferably from 120 to 180° C. As this temperature is lower, the productivity of THF tends to significantly decrease, and as the temperature is higher, the amount of a trace byproduct tends to increase.

The reaction pressure is not particularly limited but, in terms of absolute pressure, usually from 10 to 1,000 kPa, preferably from 100 to 500 kPa.

<Production Method 2>

First, the presumed mechanism of the present invention is described.

BGTF in 1,4BG is easily decomposed under acidic conditions and easily becomes 2,3DHF through OTF and 4-hydroxybutylaldehyde.

The acetal polymer resulting from polymerization of 2,3DHF produced here contains many hydroxyl groups as a functional group and becomes a kind of polyfunctional polyol under specific conditions.

In particular, when the water concentration in the reactor liquid phase is too low, a dehydration reaction of the acetal polymer above readily proceeds in the reactor, and a carbon-carbon conjugated double bond is produced. With further progress of the dehydration reaction, the acetal polymer is deprived of a hydrophilic functional group and becomes a hydrophobic polymer, as a result, solid matter precipitates in the reactor.

In addition, 2,3DHF produced by a dehydration reaction of OTF is not only formed into a polymer in the reactor but also is partially present in the vapor phase portion in the reactor and often mixed in the product THF. The reason therefor is because 2,3DHF has a boiling point of 55° C., close to the boiling point (66° C.) of THF, and can be hardly separated and removed by distillation.

For the reason above, in order to decrease the production amount of the acetal polymer, the production amount of 2,3DHF needs to be reduced. In the present invention, the concentration of OTF in the reactor liquid phase, which is a precursor of 2,3DHF, is set to a specific range, whereby the production of solid matter in the reactor liquid phase and the production amount of 2,3DHF can be reduced, so that the operation can be stably continued for a long period of time and at the same time, the load for THF purification required to remove 2,3DHF can be lowered.

The concentration of BGTF contained in the raw material 1,4BG for use in the present invention is not particularly limited but is usually from 0.001 to 5.0 wt %, preferably from 0.01 to 3.0 wt %, more preferably from 0.02 to 0.8 wt %.

If the concentration of BGTF in the raw material 1,4BG is too low, the purification of the raw material 1,4BG requires a great deal of cost, leading to an industrially undesirable tendency, whereas if the concentration of BGTF in the raw material 1,4BG is too high, solid matter may precipitate and attach to the reactor to inhibit the continuous operation.

[Production Method of Tetrahydrofuran]

The production method of THF of the present invention requires to use 1,4BG as a raw material and control the OTF concentration in the reactor liquid phase to a specific concentration range.

In the present invention, controlling the OTF concentration in the reactor liquid phase to a specific concentration range means that when the reaction start time is assumed as the time where a raw material and a catalyst are introduced into a reactor and the temperature in the reactor reaches a preset temperature and the reaction stop time is assumed as the time where the temperature in the reactor is stopped being maintained at the preset temperature (the time where heating is stopped), the operation in the portion of 70% or more of the total reaction time from the reaction start time to the reaction stop time is carried out under any one of the conditions specified above.

In the method where, as in the present invention, THF is produced by performing a cyclodehydration reaction of 1,4BG in the presence of an acid catalyst, a reaction distillation method where a catalyst is caused to exist in a reaction part, 1,4 BG is fed to the reaction part, THF produced by a cyclodehydration reaction and a byproduct containing water and OTF are drawn out from the vapor phase part of the reactor, and the liquid phase portion is kept in a state containing remaining water, a byproduct and an unreacted raw material is maintained, must be used.

The OTF concentration in the reactor liquid phase in the present invention needs to be 500 ppm by weight or less, preferably 400 ppm by weight or less, more preferably 350 ppm by weight or less, still more preferably 300 ppm by weight of less. The lower limit is not particularly limited but is preferably 1 ppm by weight or more, more preferably 5 ppm by weight or more, still more preferably 10 ppm by weight or more. As the OTF concentration in the reactor liquid phase is higher, the acetal polymer concentration rises in a short-time operation to readily cause precipitation of solid matter in the reactor and at the same time, the production amount of 2,3DHF increases. As the OTF concentration is lower, the loss of the raw material 1,4BG at the time of purification of the raw material 1,4BG or the production cost associated with purification increases.

In other words, the OTF concentration in the reactor liquid phase in the present invention is from 1 to 500 ppm by weight, preferably from 5 to 400 ppm by weight, more preferably from 7 to 350 ppm by weight, still more preferably from 10 to 300 ppm by weight. As the OTF concentration in the reactor liquid phase is higher, the acetal polymer concentration rises in a short-time operation to readily cause precipitation of solid matter in the reactor and at the same time, the production amount of 2,3DHF increases. As the OTF concentration is lower, the loss of the raw material 1,4BG at the time of purification of the raw material 1,4BG or the production cost associated with purification increases.

The specific method for controlling the OTF concentration in the reactor liquid phase to a range of 500 ppm by weight or less is not particularly limited, but the concentration can be controlled by the below-described methods or a combination of the methods. For example, in the case of using a reaction distillation type, the concentration can be controlled by a method where various conditions including the reaction temperature are altered to change the distribution coefficient based on the vapor-liquid equilibrium of OTF between the liquid phase portion and the vapor phase portion in the reactor or furthermore, the reflux ratio of a liquid obtained by discharging a gas containing THF produced by the cyclodehydration reaction and OTF from the vapor phase portion of the reactor and condensing the gas by a heat exchanger is controlled to change the flow rate ratio between THF and OTF drawn out to outside the reactor and thereby draw out OTF higher volatile than THF to outside the reactor.

In addition, as the method for controlling the OTF concentration in the reactor liquid phase, a method of adjusting the BGTF concentration in 1,4BG fed as a raw material to the reactor is considered to be effective.

In the present invention, the water concentration in the in-reactor liquid phase is usually from 1.4 to 10 wt %, preferably from 2.0 to 8.0 wt %. If the water concentration in the in-reactor liquid phase is too high, the cyclodehydration reaction is likely to be inhibited, leading to a decrease in the production rate of THF, whereas if the water concentration is too low, a dehydration reaction of the acetal polymer tends to proceed, allowing precipitation of solid matter.

In the present invention, the method for confirming the water amount in the in-reactor liquid phase is the same as that in Production Method 1 above.

The specific method for adjusting the water concentration in the reactor to a specific range is not particularly limited, but, for example, the below-described methods or a combination of the methods may be used. In the case of using a reaction distillation apparatus, the reaction temperature or various conditions are controlled to change the rate of water production resulting from the cyclodehydration reaction of 1,4BG in the reactor liquid phase or the distribution coefficient based on the vapor-liquid equilibrium of water between the liquid phase portion and the vapor phase portion in the reactor, whereby the water amount in the reactor can be controlled to a specific range. In addition, the reflux ratio of a liquid obtained by discharging a gas containing THF produced by the reaction and water from the vapor phase portion of the reactor and condensing the gas by a heat exchanger is controlled to change the flow rate ratio between THF and water drawn out to outside the reactor, whereby water less volatile than THF can be retained in the reactor and the water amount can be controlled to a specific range. Furthermore, the water amount can also be controlled to a specific range by continuously or intermittently supplying water from outside the system.

The reactor employed in the production of THF of the present invention is used interchangeably with a reaction tank, a reaction vessel, a reaction oven, a reaction column, etc.

and is not particularly limited as long as it is a vessel capable of performing a cyclodehydration reaction. In the case where the cyclodehydration reaction reaches chemical equilibrium, the reaction is allowed to proceed by removing water produced by the reaction from the reactor and therefore, the reactor preferably has a structure including therein an in-reactor liquid phase portion where a raw material, a catalyst or a product is present in liquid phase to perform a reaction, and a vapor phase portion composed of a highly volatile product. The product is continuously or intermittently drawn out from the vapor phase portion to outside the reactor according to the progress of reaction, whereby the reaction proceeds.

In the present invention, in the method of drawing out the vapor phase portion containing OTF to outside the reactor, the ratio of the weight of OTF contained in the vapor phase to the total weight of OTF contained in the liquid phase and the vapor phase is usually from 10 to 70%, preferably from 20 to 60%.

If the ratio above is too high, not only OTF but also an unreacted raw material or other impurities are likely to be contained in the vapor phase portion, leading to an industrially undesirable tendency, whereas if the ratio is too low, the OTF concentration in the in-reactor liquid phase tends to be hardly controlled.

The catalyst for use in the present invention is not particularly limited as long as it is an acid catalyst, but an acid catalyst having a pKa value of 4 or less is preferably used. The acid catalyst includes, usually, a heterogeneous acid catalyst such as cation exchange resin, sulfonated zirconia and fluorosulfonic acid-containing resin (e.g., Nafion (registered trademark, DuPont)), and a homogeneous catalyst such as sulfuric acid, nitric acid, phosphoric acid, heteropolyacid (phosphotungstic acid, phosphomolybdic acid, silicotungstic acid) and sulfonic acid compound, and a homogeneous catalyst is preferably used. Among homogeneous catalysts, from the standpoint that the catalytic activity or use temperature range is wide and the handling is easy and simple, a sulfonic acid is more preferred, and an organic sulfonic acid is still more preferred. Specific examples of the organic sulfonic acid include an aromatic sulfonic acid derivative such as para-toluenesulfonic acid, benzenesulfonic acid, ortho-toluenesulfonic acid and meta-toluenesulfonic acid, and a chain hydrocarbon sulfonic acid derivative such as methanesulfonic acid, butanesulfonic acid, hexanesulfonic acid, octanesulfonic acid and nonanesulfonic acid. These acids may be used singularly or plurally or may contain, in the carbon skeleton, a functional group other than a sulfonic acid. Among these specific examples, para-toluenesulfonic acid is preferred.

Incidentally, the reaction may be started by previously causing the catalyst to exist in the reaction part of the reactor before feeding the raw material 1,4BG and starting the reaction, but from the standpoint of suppressing the reduction in the reaction yield due to deterioration of the catalyst, it is more effective to successively charge the catalyst into the reactor. Among these, the catalyst is preferably dissolved in water, 1,4BG or THF and intermittently or continuously fed to the reactor by supplying the solution into the reactor.

As for the cyclodehydration reaction in the production of THF of the present invention, the reaction is performed while heating the reactor, and the heating system of the reactor may be a system where a heat medium such as steam is brought into contact with an external jacket to perform heating or may be a system where a heat transfer device such as coil is provided inside the reactor to perform heating. The heating system may also be a system where a heat exchanger is provided outside the reactor and the liquid phase portion of the reactor is partially drawn out to outside the system, then heated by the heat exchanger and again returned to the reactor, thereby performing heating. The material for the interior of such a reactor or heat exchanger is not particularly limited and a known material may be used, but the material includes SUS, Hastelloy (registered trademark), titanium, and glass. Among others, from the standpoint that corrosion due to sulfur contained in sulfonic acid can be reduced, SUS304, SUS316, SUS316L, SUS317, SUS317L, SUS329J4L, Hastelloy (registered trademark), titanium, and glass are preferred, and SUS316L, SUS317L, SUS329J4L, Hastelloy (registered trademark), etc. are more preferred.

In the reactor for use in the present invention, an agitator for uniformly and efficiently performing the cyclodehydration reaction is preferably provided. A mixing method equivalent to an agitator may also be used as long as the reactivity is not impaired. The agitator is not particularly limited but usually consists of an electric motor, a shaft and a stirring blade, and the stirring blade is not limited in its shape. The mixing method equivalent to an agitator is also not particularly limited and includes, for example, a method where a gas inert to the reaction is supplied to the liquid phase portion, a method where the liquid phase portion is partially drawn out to outside the system and again returned to the reactor, and a mixing method utilizing convection inside the reactor.

In the vapor phase portion of the reactor, a gas containing THF produced in the reaction part inside the reactor and water is present, and the gas may be introduced into a heat exchanger and condensed/liquefied in the heat exchanger to obtain a condensate containing tetrahydrofuran and water. The heat exchanger above is a device for condensing/liquefying a distillate occurring from the reactor, and the condensation/liquefaction is performed by exchanging heat between the distillate and an external fluid that is a cooling liquid. Incidentally, the gas containing THF and water may contain product water from a raw material charged in the form of an aqueous solution, a dehydration solvent used, if desired, for azeotroping with product water, and the like.

Incidentally, a distillation column, such as packed column and plate column, for separating high-boiling-point components, such as raw material 1,4-butanediol, from the gas containing produced THY and water may be provided before introduction into a heat exchanger. The number of plates of the packed column, plate column, etc. may be arbitrary but is usually, in terms of theoretical plates, from 1 to 100, preferably from 1 to 10, more preferably from 1 to 5, still more preferably from 1 to 4. If an excessively large number of theoretical plates are used, the column becomes too large, and the economic efficiency for construction of the facility may be reduced.

The material for the interior of such a distillation column or heat exchanger is not particularly limited and a known material may be used, but since corrosion by an acid catalyst is lessened compared to the reactor, the material includes SUS304, SUS316, SUS316L, etc.

The reaction distillation apparatus in the present invention is a device fabricated by combining an agitation-type reactor and a rectifier into one unit, and a gas yielded by partially or entirely drawing out a product present in the vapor phase portion in the reactor is fed to a distillation column such as packed column and plate column, whereby a reaction product can be obtained. In addition, a condensate obtained by cooling the gas above may be partially circulated as reflux flow into the reactor so that an unreacted raw material and the reaction product can be separated.

In the case of performing the present invention by using a reaction distillation apparatus, it is preferred that a gas containing produced THF and water is discharged from the vapor phase portion of the reactor and condensed by a heat exchanger and a condensate is obtained from the outlet of the heat exchanger and partially returned to the vapor phase portion in the reactor. The composition of the condensed liquid contains THF and water at arbitrary concentrations, but the THF concentration is usually from 30 to 99 wt %, preferably from 30 to 95 wt %, more preferably from 50 to 85 wt %, still more preferably from 50 to 75 wt %. In addition, the cyclodehydration reaction of the present invention produces water stoichiometrically, and the water concentration in the condensate is usually from 1 to 50 wt %, preferably from 5 to 30 wt %, more preferably from 15 to 25 wt %.

In the case of performing the present invention by using a reaction distillation apparatus, while the condensate obtained from the outlet of the heat exchanger is partially returned to the vapor phase portion in the reactor, the remaining condensate is drawn out to outside the reactor, and the weight ratio of the flow rate of the condensate drawn out to outside the reactor to the flow rate of the condensate fed to the vapor phase portion of the reactor (hereinafter, sometimes referred to as "reflux ratio") is usually from 0.01 to 4.0, preferably from 0.05 to 1.0, more preferably from 0.08 to 0.8. If the reflux ratio is too high, the cost of a heat source for heating is increased to deteriorate the economic efficiency and at the same time, OTF cannot be sufficiently separated from inside the reactor, leading to a tendency of the production amount of 2,3DHF to increase. If the reflux ratio is too low, the effect of suppressing precipitation of solid matter in the reactor is not obtained and at the same time, high-boiling-point components are not separated sufficiently and tend to be often mixed into the condensate. The temperature at the time of introduction of a gas containing THF and water into the heat exchanger is usually from 10 to 200° C., preferably from 60 to 100° C.

In the present invention, the reaction of producing THF by cyclodehydration of 1,4BG proceeds in the reaction part in the reactor, and the concentration of the catalyst in the liquid phase portion in the reactor is usually from 0.01 to 20 wt %, preferably from 0.05 to 10 wt %, more preferably from 0.2 to 5 wt %.

The temperature of the liquid phase portion in the reactor is preferably from 80 to 250° C., more preferably from 100 to 200° C., still more preferably from 120 to 180° C. As this temperature is lower, the productivity of THF tends to significantly decrease, and as the temperature is higher, the amount of a trace byproduct tends to increase.

The reaction pressure is not particularly limited but, in terms of absolute pressure, usually from 10 to 1,000 kPa, preferably from 100 to 500 kPa.

In the present invention, as described above, an acetal polymer is produced resulting from polymerization of 2,3DHF. The degree of coloration by a compound containing many conjugated double bonds, produced by dehydration of the acetal polymer, can be confirmed from the UV spectrum of the reactor liquid phase. The measurement wavelength region is not particularly limited but is preferably one or more wavelengths selected from the range of 300 to 330 run at the time of operation of performing a cyclodehydration reaction for less than 100 hours, and one or more wavelengths selected from the range of 650 to 750 nm at the time of operation for a long time of 100 hours or more. To rise in the absorbance at a specific wavelength is to prove the production of a long-chain compound containing many conjugated double bonds and indicates that the acetal polymer concentration in the reactor is increased and the solid matter occurring with the progress of a dehydration reaction of the acetal polymer is likely to precipitate.

The method for more quantitatively determining the production level of the carbon-carbon conjugated system due to dehydration of the acetal polymer from the UV spectrum includes a method where each of solutions in the reactor liquid phases having different absorbances is heated and a linear approximate equation of UV spectral value-solid matter quantity is prepared from the weights of the obtained dry solid matter.

From the concentration of solid matter contained in the in-reactor liquid phase and the solubility of solid matter, which are obtained by the approximate equation above, the time until the concentration of solid matter contained in the in-reactor liquid phase is saturated by exceeding the solubility of solid matter at an arbitrarily set temperature in the reactor, that is, the precipitation start time, can also be calculated. In the present invention, the precipitation start time is usually 4 hours or more, preferably 5 hours or more, more preferably 10 hours or more, still more preferably 13 hours of more. If the precipitation start time is too short, precipitation of solid matter leads to inhibition of the reaction, fouling of the heat exchanger, or clogging of the pipe, making the continuous operation difficult.

The invention according to <Production Method 1> and the invention according to <Production Method 2> are independent from each other and if the invention satisfies either one, the object of the present invention can be attained. In addition, an invention satisfying the requirements in both <Production Method 1>and <Production Method 2>is also a preferred embodiment of the present invention.

EXAMPLES

The present invention is described in greater detail below by referring to Examples, but the present invention is not limited to these Examples as long as its gist is observed.

In the following Examples, the analysis of water was performed using the Karl Fischer method. The analysis of an organic component was performed by gas chromatography (apparatus: manufactured by Shimadzu Corporation, model number: GC-2014, column: DB-1), and the ratio of the component was calculated from the area percentage. More specifically, a value after deduction of the water concentration from 100 wt % was calculated, and the ratio (wt %) of the remaining component was calculated from the obtained value based on the area percentage of each component in gas chromatography. The absorbance at 310 nm was measured by "UV-2400" manufactured by Shimadzu Corporation (using a synthetic quartz-made closed cell having a light path length of 1 mm and a light path width of 10 mm). At this time, pure water was used for blank measurement.

As for the liquid viscosity, the viscosity at a liquid temperature of 25° C. was measured at 100 rpm by using an EH type viscometer, Model Viscometer TV-22, manufactured by Told Sangyo Co., Ltd. and using cone-plate of 3°×14 mmR.

<Reference Examples 1 to 5: Preparation of Approximate Equation of UV Spectral Value-Solid Matter Yield>

<Preparation Method of Solution in In-Reactor Liquid Phase>

A glass-made 300 ml reactor was used, a column having 4 theoretical plates and packed with an irregular filler was disposed on the tank top, and a cooling tube for cooling the produced gas by a condenser serving as a heat exchanger was used at the column top. Nybrine (MORESCO Corporation, registered trademark) was used as the refrigerant, and an oil bath was used for heating the reactor. As the raw material, 1,4BG containing from 0.037 to 0.248 wt % of BGTF was used. The reactor was charged with 70 g of each raw material 1,4BG and 0.28 g (0.4 wt %) of para-toluenesulfonic acid and heated using the oil bath to raise the inner temperature of the liquid phase portion in the reactor to 150° C. After the inner liquid temperature was stabilized at 150° C., a condensate obtained by condensing a gas containing THF produced by the reaction and water in a condenser was drawn out as a product liquid into a storage tank outside the reactor. The inner temperature of the cooler region was 90° C. A cyclodehydration reaction of 1,4BG was continuously performed under these conditions to produce THF, and a condensate containing water and THF discharged as a product gas from the vapor phase portion of the reactor and condensed by a cooler was obtained at 40 g/hr and drawn out to the storage tank outside the reactor. In addition, the raw material 1,4BG was continuously fed at 40 g/hr to the reactor so as to adjust the liquid-phase amount to 70 g and thereafter, keep the liquid-phase amount constant. The amount drawn out from the liquid phase portion of the reactor was set to 0.0 g/hr and thus, none was discharged. The flow rate ratio of the raw material 1,4BG to the volume of the liquid phase portion was 3.5 times (in terms of the residence time, 3.5 hours). At this time, para-toluenesulfonic acid was dissolved in the raw material 1,4BG to afford an amount of 0.8 mg/hr and added together continuously. After passing of 90 hours since the start of reaction, feed of the raw material 1,4BG was stopped. The absorbance at 310 nm of the solution in the in-reactor liquid phase here was measured.

<Desiccation Method of Solution in In-Reactor Liquid Phase>

20 g of the solution in the in-reactor liquid phase prepared by the experiment above was put in a watch glass and heated using a hot plate. The yield of solid matter was determined from the amount of the residue after heating at a wall temperature of 150° C. for about 2 hours and heating at 250° C. for about 1 hour.

<Linear Approximate Equation of UV Spectral Value-Solid Matter Quantity>

The UV spectrum value of the solution in the in-reactor liquid phase obtained by the method above and the yield of the solid matter obtained by the desiccation treatment are shown in Table 1, and the linear approximate equation obtained from these results is shown in FIG. 1.

<Solubility of Solid Matter>

A mixed solution of 50 wt % of 1,4BG and 50 wt % of polytetramethylene ether glycol (molecular weight: 2,000, produced by Mitsubishi Chemical Corporation) was used as a model liquid of the liquid in the reaction solution, and the solubility of solid matter for this model solution was measured. The model solution and the solid matter were mixed to afford a solid matter concentration of 3.0 wt %, 5.3 wt %, 7.1 wt %, 9.6 wt % or 12.6 wt % and heated to 180° C. or more and thereafter, by gradually lowering the temperature, the temperature at which solid matter precipitates was confirmed with an eye and defined as the saturation temperature.

A linear approximate equation was derived from the saturation temperature and the solid matter concentration, and the solubility at a specific temperature was determined. The solubility of solid matter in the present invention was 10.47 wt % at 145° C.

<Precipitation Start Time>

After the amount of change in the solid matter concentration per hour was determined from the concentration in terms of solid matter and the reaction time, the reaction time required until exceeding the solubility of solid matter was determined from the amount of change in the solid matter concentration per hour and defined as the precipitation start time.

In the present invention, the solubility (10.47 wt %) at 145° C. was used as the solubility of solid matter.

TABLE 1

| | BGTF Concentration in Raw Material wt % | UV Absorbance (310 nm) | Yield of Solid Matter After Desiccation wt % |
|---|---|---|---|
| Reference Example 1 | 0.037 | 0.07 | 1.0 |
| Reference Example 2 | 0.117 | 0.46 | 2.5 |
| Reference Example 3 | 0.126 | 0.31 | 2.1 |
| Reference Example 4 | 0.128 | 0.34 | 2.1 |
| Reference Example 5 | 0.248 | 1.08 | 3.9 |

Example 1-1

A glass-made 200 cc flask reactor equipped with a glass-made cooling tube for distilling off a gas in the reactor and a raw material introduction tube was charged with 70 g of 1,4BG previously containing 0.394 wt % of BGTF and 0.28 g (0.4 wt % based on the 1,4BG solution in the flask) of para-toluenesulfonic acid (pKa value: −2.8) and heated using an oil bath until the temperature in the flask reactor (preset temperature) reaches 140° C., whereby a cyclodehydration reaction was started. The reaction temperature was atmospheric pressure. After the liquid temperature in the flask reactor was stabilized at 140° C., a gas containing the product THF and water was discharged from the vapor phase portion in the flask through a cooling tube at 87° C. and further condensed in the cooler, and a condensate containing THF was drawn out at 7.5 g/hr. At the same time, a mixed solution of the raw material 1,4BG having the same composition as that of the raw material introduced into the reactor and a para-toluenesulfonic acid was continuously supplied to the flask at the same introduction rate as the extraction rate through the raw material introduction tube so as to keep the liquid-phase amount in the flask constant. The mixed solution above was supplied after dissolving, in the raw material 1,4BG, a para-toluenesulfonic acid to afford a continuous additional amount of 20 ppm by weight.

As for the reaction conditions, the average residence time of the raw material 1,4BG in the flask relative to the liquid volume in the flask was 9.3 hours, and the composition of the obtained condensate contained 78 wt % of THF, 22 wt % of water and 1,000 ppm by weight or less of impurities.

Under the conditions above, a cyclodehydration reaction of 1,4BG, distillation of a gas containing the product THF from the vapor phase portion in the flask, and feed of the raw material 1,4BG were continued for 40 hours (reaction time T=40 hours) by keeping the temperature at 140° C.

During this operation, the reaction was performed by not drawing out liquid from the liquid phase portion in the flask but storing the entire amount of liquid in the flask. The concentration of para-toluenesulfonic acid contained in the liquid in the reactor was started from 0.40 wt % and increased to 0.43 wt % until a stoppage.

The BGTF cumulative weight (B) at the completion of reaction was 1.53 g, the water concentration of liquid in the reactor was 6.5 wt % (W is 4.4 g), and the value of O represented by formula (1) was 0.009.

The absorbance at 310 nm of the liquid in the reactor was measured, as a result, the absorbance was 0.34. Precipitation was not observed in the reactor as well as in the liquid in the reactor, and the liquid was colored pale yellow. The concentration in terms of solid matter in the in-reactor liquid phase calculated from the absorbance by using the approximate equation determined in Reference Examples was 1.5 wt %, and the precipitation start time determined from the concentration in terms of solid matter and the solubility of solid matter was 286 hours.

The results are shown in Table 2.

Example 1-2

THF was produced by performing a cyclodehydration reaction of 1,4BG in exactly the same manner as in Example 1-1 except that in Example 1-1, the temperature in the flask (preset temperature) was changed to 160° C. and the extraction rate of the condensate containing THF and the introduction rate of the raw material 1,4BG into the reactor were changed to afford an average residence time of 3.5 hours. The composition of the obtained condensate contained 81 wt % of THF, 19 wt % of water, and 1,000 ppm by weight or less of impurities. The reaction was continued for 18.5 hours (reaction time T=18.5).

The BGTF cumulative weight (B) at the completion of reaction was 1.55 g, the water concentration of liquid in the reactor was 4.8 wt % (the in-reactor water weight (W) is 3.2 g), the value of O of formula (1) was 0.026, and the absorbance at 310 nm of the liquid in the reactor was 0.49. Precipitation was not observed in the reactor as well as in the liquid in the reactor, and the liquid was colored yellow. The results are shown in Table 2. The concentration in terms of solid matter in the in-reactor liquid phase calculated from the absorbance by using the approximate equation determined in Reference Examples was 2.2 wt %, and the precipitation start time determined from the concentration in terms of solid matter and the solubility of solid matter was 88 hours.

Example 1-3

THF was produced by performing a cyclodehydration reaction of 1,4BG in exactly the same manner as in Example 1-1 except that in Example 1-1, the temperature in the flask (preset temperature) was changed to 180° C. and the extraction rate of the condensate containing THF and the introduction rate of the raw material 1,4BG into the reactor were changed to afford an average residence time of 0.9 hours. The composition of the obtained condensate contained 80 wt % of THF, 20 wt % of water, and 1,000 ppm by weight or less of impurities. The reaction was continued for 4.3 hours (reaction time T=4.3).

The BGTF cumulative weight (B) at the completion of reaction was 1.72 g, the water concentration of liquid in the reactor was 1.9 wt % (the in-reactor water weight (W) is 1.3 g), the value of O of formula (1) was 0.308, and the absorbance at 310 nm of the liquid in the reactor was 0.83. Precipitation was not observed in the reactor as well as in the liquid in the reactor, the liquid was colored dark brown, and the transparency was also reduced. The results are shown in Table 2. The concentration in terms of solid matter in the in-reactor liquid phase calculated from the absorbance by using the approximate equation determined in Reference Examples was 3.8 wt %, and the precipitation start time determined from the concentration in terms of solid matter and the solubility of solid matter was 12 hours.

Example 1-4

A system having an SUS316L-made 500 L reactor and having, on the tank top, a column including 4 theoretical plates and packed with an irregular filler was used, where the produced gas was cooled by a condenser serving as a heat exchanger at the column top. Water was used as the refrigerant for cooling, and a jacket-type heating medium (oil) was used for heating the reactor. The reactor was charged with 400 L of the raw material 1,4BG containing 0.2 wt % of BGTF and 800 g (0.2 wt %) of para-toluenesulfonic acid and heated using the heating medium to raise the inner temperature (preset temperature) of the liquid phase portion in the reactor to 145° C. After the inner liquid temperature was stabilized at 145° C., a condensate obtained by condensing a gas containing THF produced by the reaction and water in a condenser was drawn out as a product liquid into a storage tank outside the reactor and at the same time, partially again introduced as a liquid into below the cooler at the top of the reactor to undergo refluxing. The inner temperature of the cooler region was 87° C.

A cyclodehydration reaction of 1,4BG was continuously performed under the conditions above to produce THF. A condensate containing water and THF discharged as a product gas from the vapor phase portion of the reactor and condensed by a cooler was obtained at 60 kg/hr and while a 15 kg/hr part thereof was fed to the vapor phase portion of the reactor, the remaining was drawn out to the storage tank outside the reactor (reflux ratio: 0.3). In addition, the raw material 1,4BG was continuously fed at 60 kg/hr to the reactor so as to adjust the liquid-phase amount to 360 L and thereafter, keep the liquid-phase amount constant. The amount drawn out from the liquid phase portion of the reactor was set to 0.0 kg/hr and thus, none was discharged. The flow rate ratio of the raw material 1,4BG to the volume of the liquid phase portion was 6 times (in terms of the residence time, 6 hours). At this time, para-toluenesulfonic acid was dissolved in the raw material 1,4BG to afford an amount of 0.72 g/hr and added together continuously. Here, the water concentration of the liquid phase portion of the reactor was 2.72 wt %.

The composition of the condensate obtained in the storage tank contained 80 wt % THF and 20 wt % of water, in which the amount of 1,4BG was at or below the detection lower limit of 10 ppm by weight.

After passing of 40 hours since the start of reaction, feed of the raw material 1,4BG was stopped. At this time, the BGTF cumulative weight (B) was 5,655 g, the water weight (W) of liquid in the reactor was 7,888 g, and the value of θ represented by formula (1) was 0.018. The absorbance at 310 nm of the liquid in the reactor was measured, as a result, the absorbance was 0.40. Precipitation was not observed in the reactor as well as in the liquid in the reactor, and the liquid was colored yellow. the results are shown in Table 2. The concentration in terms of solid matter in the in-reactor liquid phase calculated from the absorbance by using the approximate equation determined in Reference Examples was 1.8 wt %, and the precipitation start time determined from the concentration in terms of solid matter and the solubility of solid matter was 238 hours.

Comparative Example 1-1

In Example 1-1, the cyclodehydration reaction of 1,4BG was performed to produce THF by changing the temperature in the flask (preset temperature) to 110° C., but the average residence time was as large as 613 hours, and THF could not be substantially produced.

Comparative Example 1-2

THF was produced by performing a cyclodehydration reaction of 1,4BG in exactly the same manner as in Example 1-1 except that in Example 1-1, the temperature in the flask (preset temperature) was changed to 210° C. and the extraction rate of the condensate containing THF and the introduction rate of the raw material 1,4BG into the reactor were changed to afford an average residence time of 0.27 hours. The composition of the obtained condensate contained 81 wt % of THF, 19 wt % of water, and 1,000 ppm by weight or less of impurities. The reaction was continued for 1.5 hours (reaction time T=1.5).

The BGTF cumulative weight (B) at the completion of reaction was 1.81 g, the water concentration of liquid in the reactor was 1.3 wt % (the in-reactor water weight (W) is 1.0 g), the value of θ of formula (1) was 1.207, and the absorbance at 310 nm of the liquid in the reactor was 1.013. Precipitation was not observed in the reactor as well as in the liquid in the reactor, the liquid was colored dark blown, and the transparency was also reduced. The results are shown in Table 2. The concentration in terms of solid matter in the in-reactor liquid phase calculated from the absorbance by using the approximate equation determined in Reference Examples was 4.7 wt %, and the precipitation start time determined from the concentration in terms of solid matter and the solubility of solid matter was 3 hours.

TABLE 2

|  |  |  | Comparative Example 1-1 | Example 1-1 | Example 1-2 | Example 1-3 | Comparative Example 1-2 | Example 1-4 |
|---|---|---|---|---|---|---|---|---|
| Reaction Conditions | Reaction temperature | [° C.] | 110 | 140 | 160 | 180 | 210 | 145 |
|  | Average residence time | [hr] | 613 | 9.3 | 3.5 | 0.9 | 0.27 | 6 |
|  | Composition of condensate | THF [wt %] | — | 78 | 81 | 80 | 81 | 80 |
|  |  | Water [wt %] | — | 22 | 19 | 20 | 19 | 20 |
|  | BGTF Concentration in raw material 1,4BG | [wt %] | 0.448 | 0.394 | 0.394 | 0.394 | 0.448 | 0.2 |
|  | Eater concentration of liquid in reactor | [wt %] | 12.3 | 6.5 | 4.8 | 1.9 | 1.3 | 2.72 |
| Reaction time T [hr] |  |  | — | 40 | 18.5 | 4.3 | 1.5 | 40 |
| BGTF cumulative amount B [g] |  |  | — | 1.53 | 1.55 | 1.72 | 1.81 | 5655 |
| Water weight W [g] |  |  | — | 4.4 | 3.2 | 1.3 | 1 | 7888 |
| θ of formula (1) |  |  | — | 0.009 | 0.026 | 0.308 | 1.207 | 0.018 |
| State of liquid in reactor | UV 310 nm absorbance |  | — | 0.34 | 0.49 | 0.83 | 1.013 | 0.40 |
|  | Color |  | — | pale yellow | yellow | dark brown | dark brown | yellow |
|  | Solid matter |  | — | none | none | none | none | none |

TABLE 2-continued

|  |  | Comparative Example 1-1 | Example 1-1 | Example 1-2 | Example 1-3 | Comparative Example 1-2 | Example 1-4 |
|---|---|---|---|---|---|---|---|
| Concentration in terms of solid matter (wt %) |  | — | 1.5 | 2.2 | 3.8 | 4.7 | 1.8 |
| Precipitation start time (h) |  | — | 286 | 88 | 12 | 3 | 238 |
| Distillate | g/hr | 0.11 | 7.53 | 20.00 | 77.78 | 259.26 | 11.67 |

Example 2-1

A glass-made 1,200 cc flask reactor was charged with 1,000 g of 1,4BG containing 0.28 wt % of BGTF and 2 g (0.2 wt % based on 1,4BG in the flask) of para-toluenesulfonic acid (pKa value: -2.8), and a cyclodehydration reaction was performed by batch reaction distillation by setting the pressure at the top to ordinary pressure and the temperature of the liquid phase portion (preset temperature) to 145° C. and using an Oldershaw distillation column with a column diameter of 35 mm having 5 theoretical plates. At this time, the reflux ratio was set to 0.1. After the temperature of the liquid phase portion was stabilized, the reaction was performed for about 3 hours, a gas containing the product THF and water discharged from the top was condensed by a condenser, and 740 g of a condensate containing THF was drawn out. In this condensate, 0.02 g (17 ppm by weight) of 2-hydroxytetrahydrofuran and 0.03 g (37 ppm by weight) of 2,3-dihydrofuran were contained. In the reactor, 100 g of a concentrated solution remained, and 0.02 g (120 ppm by weight) of 2-hydroxytetrahydrofurn was contained in the concentrated solution. At this time, the ratio of the OTF concentration by weight in the condensate to the concentration by weight of OTF contained in the concentrated solution (hereinafter, sometimes referred to as "OTF ratio") was 14.2%. The absorbance at 310 nm of the concentrated solution was measured, as a result, the absorbance was 0.17. Precipitation was not observed in the reactor as well as in the liquid in the reactor, and the liquid was pale yellow. The results are shown in Table 3. The concentration in terms of solid matter in the in-reactor liquid phase calculated from the absorbance by using the approximate equation determined in Reference Examples was 1.01 wt %, and the precipitation start time determined from the concentration in terms of solid matter and the solubility of solid matter was 31 hours.

Example 2-2

A cyclodehydration reaction was performed under the same conditions as in Example 2-1 except that the raw material was changed to 1,4BG having a BGTF concentration of 0.59 wt %. After the temperature of the liquid phase portion was stabilized, the reaction was performed for about 3 hours, a gas containing the product THF and water discharged from the top was condensed by a condenser, and 740 g of a condensate containing THF was drawn out. In this condensate, 0.02 g (25 ppm by weight) of 2-hydroxytetrahydrofuran and 0.04 g (50 ppm by weight) of 2,3-dihydrofuran were contained. In the reactor, 227 g of a concentrated solution remained, and 0.06 g (260 ppm by weight) of 2-hydroxytetrahydrofurn was contained in the concentrated solution. At this time, the OTF ratio was 9.6%. The absorbance at 310 nm of the concentrated solution was measured, as a result, the absorbance was 0.16. Precipitation was not observed in the reactor as well as in the liquid in the reactor, and the liquid was pale yellow. The results are shown in Table 3. The concentration in terms of solid matter in the in-reactor liquid phase calculated from the absorbance by using the approximate equation determined in Reference Examples was 0.96 wt %, and the precipitation start time determined from the concentration in terms of solid matter and the solubility of solid matter was 33 hours.

Example 2-3

A cyclodehydration reaction was performed under the same conditions as in Example 2-1 except that the raw material was changed to 1,4BG having a BGTF concentration of 1.13 wt %. After the temperature of the liquid phase portion was stabilized, the reaction was performed for about 3 hours, a gas containing the product THF and water discharged from the top was condensed by a condenser, and 740 g of a condensate containing THF was drawn out. In this condensate, 0.04 g (55 ppm by weight) of 2-hydroxytetrahydrofuran and 0.07 g (100 ppm by weight) of 2,3-dihydrofuran were contained. In the reactor, 227 g of a concentrated solution remained, and 0.08 g (336 ppm by weight) of 2-hydroxytetrahydrofurn was contained in the concentrated solution. At this time, the OTF ratio was 16.4%. The absorbance at 310 nm of the concentrated solution was measured, as a result, the absorbance was 0.54. Precipitation was not observed in the reactor as well as in the liquid in the reactor, and the liquid was yellow. The results are shown in Table 3. The concentration in terms of solid matter in the in-reactor liquid phase calculated from the absorbance by using the approximate equation determined in Reference Examples was 2.80 wt %, and the precipitation start time determined from the concentration in terms of solid matter and the solubility of solid matter was 11 hours.

Comparative Example 2-1

A cyclodehydration reaction was performed under the same conditions as in Example 2-1 except that the raw material was changed to 1,4BG having a BGTF concentration of 2.84 wt % and an Oldershaw distillation column having 1 theoretical plate was used. After the temperature of the liquid phase portion was stabilized, the reaction was performed for about 3 hours, a gas containing the product THF and water discharged from the top was condensed by a condenser, and 740 g of a condensate containing THF was drawn out. In this condensate, 0.12 g (161 ppm by weight) of 2-hydroxytetrahydrofuran and 0.14 g (190 ppm by weight) of 2,3-dihydrofuran were contained. In the reactor, 227 g of a concentrated solution remained, and 0.11 g (507 ppm by weight) of 2-hydroxytetrahydrofurn was contained in the concentrated solution. At this time, the ratio of the OTF concentration by weight in the condensate to the concentration by weight of OTF contained in the concentrated solution (hereinafter, sometimes referred to as "OTF ratio") was 31.8%. The absorbance at 310 nm of the concentrated solution was measured, as a result, the absorbance was 2.16. Precipitation was not observed in the reactor as well as in the liquid in the reactor, and the liquid was brown. The results are shown in Table 3. The concentration in terms of solid matter in the in-reactor liquid phase calculated from the absorbance by using the approximate equation determined in Reference Examples was 10.64 wt %, and the precipitation start time determined from the concentration in terms of solid matter and the solubility of solid matter was 3 hours.

Comparative Example 2-2

A cyclodehydration reaction was performed under the same conditions as in Example 2-1 except that the raw material was changed to 1,4BG having a BGTF concentration of 2.84 wt %. After the temperature of the liquid phase portion was stabilized, the reaction was performed for about 3 hours, a gas containing the product THF and water discharged from the top was condensed by a condenser, and 740 g of a condensate containing THF was drawn out. In this condensate, 0.05 g (131 ppm by weight) of 2-hydroxytetrahydrofuran and 0.17 g (227 ppm by weight) of 2,3-dihydrofuran were contained. In the reactor, 230 g of a concentrated solution remained, and 0.24 g (625 ppm by weight) of 2-hydroxytetrahydrofurn was contained in the concentrated solution. At this time, the OTF ratio was 21.0%. The absorbance at 310 nm of the concentrated solution was measured, as a result, the absorbance was 2.57. Precipitation was not observed in the reactor as well as in the liquid in the reactor, and the liquid was brown. The results are shown in Table 3. The concentration in terms of solid matter in the in-reactor liquid phase calculated from the absorbance by using the approximate equation determined in Reference Examples was 12.64 wt %, and the precipitation start time determined from the concentration in terms of solid matter and the solubility of solid matter was 2 hours.

Comparative Example 2-3

A cyclodehydration reaction was performed under the same conditions as in Example 2-1 except that the raw material was changed to 1,4BG having a BGTF concentration of 2.84 wt % and the reflux ratio was changed to 5.0. After the temperature of the liquid phase portion was stabilized, the reaction was performed for about 3 hours, a gas containing the product THF and water discharged from the top was condensed by a condenser, and 739 g of a condensate containing THF was drawn out. In this condensate, 0.05 g (67 ppm by weight) of 2-hydroxytetrahydrofuran and 0.24 g (327 ppm by weight) of 2,3-dihydrofuran were contained. In the reaction oven, 231 g of a concentrated solution remained, and 0.19 g (855 ppm by weight) of 2-hydroxytetrahydrofurn was contained in the concentrated solution. At this time, the OTF ratio was 7.8%. The absorbance at 310 nm of the concentrated solution was measured, as a result, the absorbance was 3.65. Precipitation was not observed in the reactor as well as in the liquid in the reactor, and the liquid was brown. The results are shown in Table 3. The concentration in terms of solid matter in the in-reactor liquid phase calculated from the absorbance by using the approximate equation determined in Reference Examples was 17.87 wt %, and the precipitation start time determined from the concentration in terms of solid matter and the solubility of solid matter was 2 hours.

TABLE 3

|  |  |  | Example 2-1 | Example 2-2 | Example 2-3 | Comparative Example 2-1 | Comparative Example 2-2 | Comparative Example 2-3 |
|---|---|---|---|---|---|---|---|---|
| BGTF concentration in raw material |  | (wt %) | 0.28 | 0.59 | 1.13 | 2.84 | 2.84 | 2.84 |
| Conditions of reaction distillation apparatus | Bottom temperature | ° C. | 145 | 145 | 145 | 145 | 145 | 145 |
|  | Pressure at top | kPa abs. | 113 | 113 | 113 | 113 | 113 | 113 |
|  | Number of theoretical plates | plates | 5 | 5 | 5 | 1 | 5 | 5 |
|  | Reflux ratio | weight ratio | 0.1 | 0.1 | 0.1 | 0.1 | 0.1 | 5.0 |
| Condensate outside reactor | OTF | g | 0.02 | 0.02 | 0.04 | 0.12 | 0.05 | 0.05 |
|  |  | wt ppm | 17 | 25 | 55 | 161 | 131 | 67 |
|  | 2,3 DHF | g | 0.03 | 0.04 | 0.07 | 0.14 | 0.17 | 0.24 |
|  |  | wt ppm | 37 | 50 | 100 | 190 | 227 | 327 |
| Concentrated solution in reactor | OTF | g | 0.02 | 0.06 | 0.08 | 0.11 | 0.24 | 0.19 |
|  |  | wt ppm | 120 | 260 | 336 | 507 | 625 | 855 |
| Absorbance |  | 310 nm-abs. | 0.17 | 0.16 | 0.54 | 2.16 | 2.57 | 3.65 |
| Concentration in terms of solid matter (wt %) |  |  | 1.01 | 0.96 | 2.80 | 10.64 | 12.64 | 17.87 |
| Precipitation start time (h) |  |  | 31 | 33 | 11 | 3 | 2 | 2 |
| Color of concentrated solution in reactor |  |  | pale yellow | pale yellow | yellow | brown | pale brown | brown |
| Water amount in reactor (wt %) |  |  | 2.30 | 2.81 | 2.92 | 2.72 | 2.79 | 4.12 |

While the invention has been described in detail and with reference to specific embodiments thereof, it will be apparent to one skilled in the art that various changes and modifications can be made therein without departing from the spirit and scope thereof. This application is based on a Japanese patent application filed on Oct. 18, 2012 (Application No. 2012-231016) and a Japanese patent application filed on Jan. 29, 2013 (Application No. 2013-014415), the content thereof being incorporated herein by reference.

The invention claimed is:

1. (I) A method for producing tetrahydrofuran, comprising feeding 1,4-butanediol to a reactor and performing a cyclodehydration reaction in the presence of an acid catalyst to obtain tetrahydrofuran, wherein a water concentration in a in-reactor liquid phase is within a range of 1.4 to 10 wt %;

(II) a method for producing tetrahydrofuran, comprising feeding 1,4-butanediol containing 2-(4-hydroxybutoxy)-tetrahydrofuran to a reactor and performing a cyclodehydration reaction in the presence of an acid catalyst to obtain tetrahydrofuran, wherein a θ value of the following formula (1) is within a range of 0.001 to 0.5:

$$\theta = B/(W \cdot T) \qquad (1)$$

(in formula (1), T represents a reaction time (hr), B represents a cumulative weight (g) of 2-(4-hydroxybutoxy)-tetrahydrofuran in the reaction time T, and W represents an in-reactor liquid-phase water weight (g) in the reaction time T); or (III) a method for producing tetrahydrofuran, comprising feeding 1,4-butanediol to a reactor and performing a cyclodehydration reaction in the presence of an acid catalyst to obtain tetrahydrofuran, wherein the cyclodehydration reaction is performed by a reaction distillation method and a 2-hydroxytetrahydrofuran concentration in the in-reactor liquid phase is within a range of 500 ppm by weight or less.

2. The method for producing tetrahydrofuran as claimed in claim 1, wherein said 1,4-butanediol contains from 0.001 to 5.0 wt % of 2-(4-hydroxybutoxy)-tetrahydrofuran.

3. The method for producing tetrahydrofuran as claimed in claim 1, wherein the cyclodehydration reaction is performed by a reaction distillation method.

4. The method for producing tetrahydrofuran as claimed in claim 1, wherein said acid catalyst has a pKa value of 4 or less.

5. The method for producing tetrahydrofuran as claimed in claim 1, wherein said acid catalyst is a homogeneous acid catalyst.

6. The method for producing tetrahydrofuran as claimed in claim 1, wherein the acid catalyst concentration in said reactor liquid phase is controlled to a range from 0.01 to 20 wt %.

7. The method for producing tetrahydrofuran as claimed in claim 1, wherein the temperature of the liquid phase portion in said reactor is within a range of 80 to 250° C.

8. The method for producing tetrahydrofuran as claimed in claim 1, wherein said acid catalyst is an organic sulfonic acid.

9. The method for producing tetrahydrofuran as claimed in claim 1, further comprising a step of dissolving said acid catalyst having a pKa value of 4 or less in 1,4-butanediol, tetrahydrofuran or water and feeding the solution to the reactor.

10. The method for producing tetrahydrofuran as claimed in claim 1, wherein the viscosity at 25° C. of the solution of the liquid phase portion in said reactor is within a range of 50 to 1,300 mPa·s.

11. The method for producing tetrahydrofuran as claimed in claim 1, wherein the water concentration in the liquid phase in said reactor is within a range of 1.4 to 10 wt %.

12. The method for producing tetrahydrofuran as claimed in claim 1, wherein a gas containing tetrahydrofuran and water and existing in the vapor phase in said reactor is drawn out to outside the reactor.

13. The method for producing tetrahydrofuran as claimed in claim 1, wherein a gas containing tetrahydrofuran, water and 2-hydroxytetrahydrofuran and existing in the vapor phase in said reactor is withdrawn to the outside of the reactor.

14. The method for producing tetrahydrofuran as claimed in claim 13, wherein at the time of withdrawal of said 2-hydroxytetrahydrofuran to the outside of the reactor, the ratio of the concentration by weight of 2-hydroxytetrahydrofuran contained in the vapor phase to the concentration by weight of 2-hydroxytetrahydrofuran contained in the liquid phase is within a range of 10 to 70%.

15. The method for producing tetrahydrofuran as claimed in claim 13, wherein at the time of withdrawal of said 2-hydroxytetrahydrofuran to the outside of the reactor, the reflux ratio of the distillation column is set to within a range of 0.01 to 4.0 by using a reactor of a reaction distillation type.

* * * * *